United States Patent [19]

Kraus et al.

[11] Patent Number: 5,420,284
[45] Date of Patent: May 30, 1995

[54] PROCESS FOR THE PREPARATION OF 2-SUBSTITUTED 5-ALKYL-PYRIDINES

[75] Inventors: Helmut Kraus; Alexander Klausener, both of Cologne; Hauke Fürstenwerth, Leverkusen, all of Germany

[73] Assignee: Bayer Aktiengesellschaft, Leverkusen, Germany

[21] Appl. No.: 133,729

[22] Filed: Oct. 7, 1993

[30] Foreign Application Priority Data

Oct. 14, 1992 [DE] Germany .................. 42 34 637.1

[51] Int. Cl.$^6$ ............................................. C07D 213/61
[52] U.S. Cl. ................................... 546/250; 546/252
[58] Field of Search ............................... 546/250, 252

[56] References Cited

U.S. PATENT DOCUMENTS 3,632,807  1/1972  Maurer et al. ..................... 546/309
4,348,396  9/1982  Kierstead et al. .................. 544/252
4,386,209  5/1983  McGill et al. ..................... 546/311

(List continued on next page.)

FOREIGN PATENT DOCUMENTS 0060071  9/1982  European Pat. Off. ............ 546/306
 240010 10/1986  Germany ........................... 546/306

OTHER PUBLICATIONS

Advanced Organic Chemistry, "Reactions, Mechanisms, and Structure", Jerry March, pp. 20–22, 1985.

(List continued on next page.)

Primary Examiner—C. Warren Ivy
Assistant Examiner—Zinna N. Davis
Attorney, Agent, or Firm—Sprung Horn Kramer & Woods

[57] ABSTRACT

The title compounds of the formula

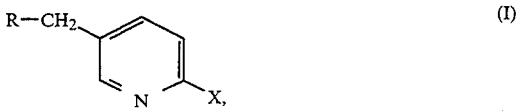

(I)

can be prepared by cyclization of aminomethylenated 2-pentenoic acid derivatives of the formula

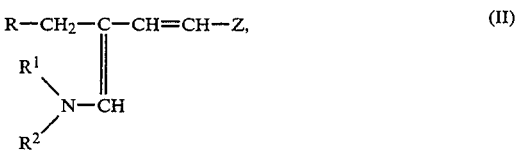

(II)

where
  R, X, $R^1$, $R^2$ and Z have the meaning given in the description,
in the presence of acids or ammonia. Preferably, aminomethylenated pentenoic acid derivatives are employed which can be prepared from pentenoic acid derivatives of the formula $$R-CH_2-CH_2-CH=CH-Z \qquad (III)$$

or $$R-CH_2-CH=CH-CH_2-Z \qquad (IV)$$

with ortho-amides of the formula

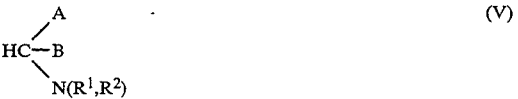

(V)

The meanings of A and B are also given in the description.

8 Claims, No Drawings

U.S. PATENT DOCUMENTS

| | | |
|---|---|---|
| 4,404,388 | 9/1983 | Fah et al. .............................. 546/346 |
| 4,405,552 | 9/1983 | Miesel .................................. 546/306 |
| 4,473,696 | 9/1984 | Hartmann et al. ................... 546/290 |
| 4,479,001 | 10/1984 | Johnston et al. .................... 546/291 |
| 4,491,468 | 1/1985 | Johnston et al. .................... 504/130 |
| 4,523,017 | 6/1985 | Johnston et al. .................... 546/302 |
| 4,551,170 | 11/1985 | Johnston et al. .................... 504/130 |
| 4,628,099 | 12/1986 | Johnston et al. .................... 546/309 |
| 4,658,031 | 4/1987 | Hartmann et al. ................... 546/193 |
| 4,687,854 | 8/1987 | Hartmann et al. ................... 546/261 |
| 4,738,924 | 4/1988 | Kulla et al. ........................... 435/121 |
| 4,753,673 | 6/1988 | Johnston et al. .................... 504/130 |
| 4,849,432 | 7/1989 | Shiokawa et al. ................... 514/341 |
| 4,897,488 | 1/1990 | Gallenkamp et al. ............... 546/345 |
| 5,010,201 | 4/1991 | Kaufmann et al. .................. 546/316 |
| 5,053,516 | 10/1991 | Hartmann et al. ................... 546/251 |

OTHER PUBLICATIONS

Chemical Abstract: 27–Heterocycles, vol. 97, 1982, p. 805; 182171q: "Novel ring opening of aminoheterocycles: . . . ", A. R. Katritzky, et al.

J. J. Baldwin et al., "Utilization of . . . Acid Derivatives", J. Org. Chem 43, pp. 2529–2535 (1978).

Abstract of JP 55/76 863, Pharmaceuticals, p. 4, Week C30, 1980.

J. Shabtai et al., "Base–Catalyzed . . . Acrylates", J. Org. Chem 46, pp. 3795–3802 (1981).

M. Prochazka et al., "Isomerization of Unsaturated Nitriles", Coll. Czech. Chem. Comm., vol. 35, pp. 1224–1234 (1970).

W. S. Johnson et al., "Stereochemistry of . . . the Litsenolides", J. Org. Chem., vol. 47, pp. 163–167 (1982).

PROCESS FOR THE PREPARATION OF 2-SUBSTITUTED 5-ALKYL-PYRIDINES

The invention relates to a process for the preparation of 2-substituted 5-alkyl-pyridines by reaction of aminomethylenated 2-pentenoic acid derivatives with acids or amines. The invention furthermore relates to the preparation of the said aminomethylenated 2-pentenoic acid derivatives.

2-Substituted 5-methyl-pyridines are important intermediates for the preparation of herbicides (EP 483), insecticides (EP 235 725) and pharmaceuticals (CA 1,189,509).

The simplest method for the synthesis of 2-substituted 5-methyl-pyridines appears in principle to be the direct functionalisation of β-picoline. Reaction with sodium amide in liquid ammonia according to Chichibabin (Tschitschibabin), however, also gives a large part of 2-amino-3-methyl-pyridine in addition to the desired isomer (U.S. Pat. No. 4,386,209). Chlorination of β-picoline-N-oxide with special chlorinating agents leads in good yield to 2-chloro-5-methylpyridine; this reaction is very complicated to carry out, however (DE-OS (German Published Specification) 3 800 179 and DE-OS (German Published Specification) 3 839 332). Until now, hydroxylation has only been described for the preparation of 6-hydroxynicotinic acid (EP 152 949); the reduction of the carboxyl group necessary for this purpose is complicated, however. On the other hand, the conversion of 2-amino- or 2-hydroxy-pyridines to the chloro derivatives has been described as being very readily carried out (GB 1,215,387; EP 72 777).

In heterocyclic syntheses, ring construction is often preferred to substitution on the basic structure. An interesting 3+3 linkage is described in EP 108 483; by reaction of morpholinopropene with acrylic acid derivatives, however, only the corresponding dihydropyridine is obtained, which then has to be aromatised with extra effort. The use of α-chloro-acrylonitrile according to EP 162 464 leads directly, but in a low yield, to 2-chloro-5-methyl-pyridine.

The 5+1 linkage, i.e. the reaction of propylidenecyanoacetic esters with dimethylformamide(DMF) acetal and subsequent cyclisation with hydrogen bromide is described as a convenient possibility for the preparation of 5-substituted 2-bromo-pyridines (J. Org. Chem. 43, 2529 (1978)) and 2-chloro-pyridines (JP 55/76 863 (1980)), where, however, the requirement exists that the 3- or 5-position is occupied by electron-withdrawing I substituents.

In view of this prior art, it is surprising that non-substituted, aminomethylenated 2-pentenoic acid derivatives can be cyclised to give 2-substituted 5-alkylpyridines.

The preparation of the said aminomethylenated 2-pentenoic acid derivatives as intermediates from non-amino-methylenated 2-pentenoic acid derivatives of the type mentioned below and ortho-amides also takes place surprisingly smoothly, since because of the molecular structure an aminomethylenation was equally to be expected in the desired γ-position as in the undesired α-position. In addition, isomerisation, dimerisation and polymerisation of the 2-pentenoic acid derivative itself were to be expected; thus J. Org. Chem. 46 (1981), 3795 describes the alkaline dimerisation of substituted acrylic esters; Coll. Czech. Chem. Commun. Vol. 35, (1970), 1224 describes the isomerisation and dimerisation of unsaturated nitriles and J. Org. Chem. 47 (1982), 163 the preferred reaction of conjugated acrylic esters in the α-position with displacement of the double bond.

The invention relates to a process for the preparation of 2-substituted 5-alkyl-pyridines of the formula

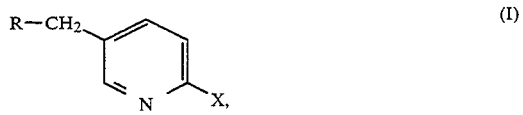

in which

R represents hydrogen or straight-chain or branched $C_1$–$C_4$-alkyl and

X denotes chlorine, bromine, hydroxyl or amino, which is characterised in that aminomethylenated 2-pentenoic acid derivatives of the formula

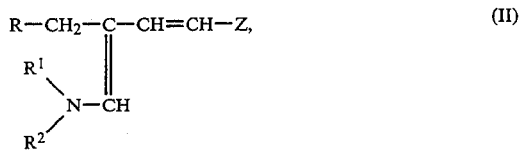

in which $R^1$ and $R^2$ independently of one another represent straight-chain or branched $C_1$–$C_8$-alkyl, $C_2$–$C_8$-alkenyl, $C_2$–$C_8$-alkoxyalkyl, $C_3$–$C_8$-alkoxyalkenyl, $C_3$–$C_8$-cycloalkyl, $C_6$–$C_{12}$-aryl, $C_7$–$C_{10}$-aralkyl or a 5- to 8-membered saturated or unsaturated heterocyclic ring, heteroatoms 1 or 2 of which are from the group consisting of N, O and S, where $R^1$ and $R^2$, together with the N atom which they substitute, can additionally form a 5- to 8-membered ring which can contain a further heteroatom from the group consisting of N, O and S, and Z represents CN or $COOR^3$, where $R^3$ denotes straight-chain or branched $C_1$–$C_8$-alkyl, $C_2$–$C_8$-alkenyl, $C_2$–$C_8$-alkoxyalkyl, $C_3$–$C_8$-alkoxyalkenyl or $C_3$–$C_8$-cycloalkyl, are cyclised in the presence or in the absence of a polar solvent at −10° C. to +25° C. in the presence of 1 to 10 mol, relative to the 2-pentenoic acid derivative, of HCl, HBr, a concentrated strong inorganic or organic non-oxidising oxygen acid or in the presence of 1 to 10 mol, relative to the butene derivative, of $NH_3$.

The invention furthermore preferably relates to the preparation of the 2-substituted 5-alkyl-pyridines, which is characterised in that an aminomethylenated 2-pentenoic acid derivative is employed which is obtained in the reaction of non-aminomethylenated 2-pentenoic acid derivatives of the formula $$R-CH_2-CH_2-CH=CH-Z \quad (III)$$

or $$R-CH_2-CH=CH-CH_2-Z \quad (IV)$$

with ortho-amides of the formula

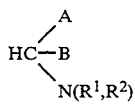

where in the formulae
R, Z, $R^1$ and $R^2$ have the abovementioned scope of meaning and
A and B independently of one another represent $OR^4$, $OR^5$, $N(R^6,R^7)$ or $N(R^8,R^9)$, wherein $R^4$, $R^5$, $R^6$, $R^7$, $R^8$ and $R^9$ independently of one another have the meaning of $R^1$ or $R^2$, the reaction being carried out in the presence or in the absence of a solvent whose acidity is lower than the C—H acidity of the 2-pentenoic acid derivative, at 50° to 200° C., 0.01 to 10 bar and at a molar ratio of 2-pentenoic acid derivative:ortho-amide = 1 to 50:1.

Straight-chain or branched $C_1$—$C_8$-alkyl is, for example, methyl, ethyl, propyl, isopropyl, butyl, isobutyl, tertbutyl, or one of the isomeric pentyls, hexyls or octyls, preferably one of the said $C_1$-$C_4$-alkyl radicals.

Straight-chain or branched $C_2$-$C_8$-alkenyl is, for example, vinyl, propenyl, allyl, or one of the isomeric butenyls, pentenyls, hexenyls or octenyls, preferably one of the said $C_3$-$C_4$-alkenyl radicals.

Straight-chain or branched $C_2$-$C_8$-alkoxyalkyl is, for example, methoxymethyl, ethoxymethyl or another radical from the group $C_3$-$C_9$-alkyl, in which a $CH_2$ group is replaced by an O atom.

Straight-chain or branched $C_3$-$C_8$-alkoxyalkenyl is, for example, methoxyvinyl, ethoxyvinyl, methoxyallyl, 2-methoxy-propenyl or another from the group consisting of $C_4$-$C_9$-alkenyl, wherein a $CH_2$ group is replaced by an O atom.

$C_3$-$C_8$-Cycloalkyl is, for example, cyclopropyl, methyl-cyclopropyl, dimethyl-cyclopropyl, cyclobutyl, methyl-cyclobutyl, cyclopentyl, methyl-cyclopentyl, cyclohexyl, methyl-cyclohexyl, dimethyl-cyclohexyl, cycloheptyl or cyclooctyl, preferably cyclopropyl, cyclopentyl and cyclohexyl, as well as their methyl or dimethyl derivatives.

$C_6$-$C_{12}$-Aryl is, for example, phenyl, naphthyl or biphenylyl, preferably phenyl.

$C_7$-$C_{10}$-Aralkyl is, for example, benzyl, 1-phenylethyl, 2-phenylethyl or another radical of this type known to the person skilled in the art, preferably benzyl.

A 5- to 8-membered saturated or unsaturated heterocyclic ring which may be mentioned, the heteroatoms 1 or 2 of which are from the group consisting of N, O and S is: pyrrole, furan, thiophene, pyrrolidine, pyrroline, pyrazole, imidazole, thiazole, oxazole, pyridine, pyrimidine, piperazine, morpholine, pyran, azepine, azocine, isoxazole, isothiazole, pyridazine and pyrazine, which can be substituted on the N atom by $C_1$-$C_4$-alkyl or by hydroxy-$C_1$-$C_4$-alkyl.

It is known to the person skilled in the art that unsaturated heterocyclic rings can have aromatic character which is pronounced to a greater or lesser extent. Heterocyclic rings of this type which may be preferably mentioned are morpholine, pyrrolidine and piperidine, which can be substituted by $C_1$-$C_4$-alkyl or by hydroxy-$C_1$-$C_4$-alkyl.

Furthermore, $R^1$ and $R^2$, together with the N atom which they substitute, can form a 5- to 8-membered saturated or unsaturated ring, which can contain a further heteroatom from the group consisting of N, O and S. Rings of this type are, for example, the abovementioned heterocycles.

R is preferably hydrogen.

The substituents $R^{11}$ and $R^{12}$, which independently of one another denote straight-chain or branched $C_1$-$C_8$-alkyl, cyclopropyl, cyclopentyl, cyclohexyl, phenyl or benzyl, furthermore preferably take the place of $R^1$ and $R^2$, it furthermore being possible for $R^{11}$ and $R^{12}$, together with the N atom which they substitute, to form a 5- to 6-membered ring which can contain a further heteroatom from the group consisting of N, O and S.

The substituents $R^{21}$ and $R^{22}$, which independently of one another denote straight-chain or branched $C_1$-$C_4$-alkyl, particularly preferably take the place of $R^{11}$ and $R^{12}$, it furthermore being possible for $R^{21}$ and $R^{22}$, together with the N atom which they substitute, to denote morpholine, pyrrolidine or piperidine, which can be substituted by $C_1$-$C_4$-alkyl or by hydroxy-$C_1$-$C_4$-alkyl.

The ortho-amides which can be employed according to the invention include DMF acetals, aminal esters and triaminomethanes of the formulae

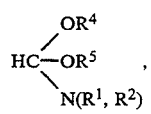

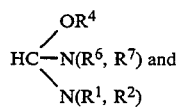

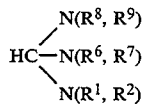

The reactions according to the invention can be represented by way of example as follows:

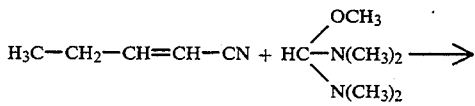

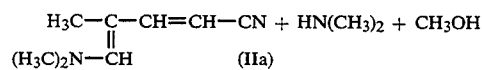

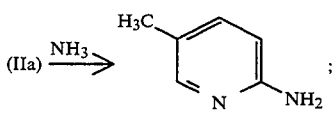

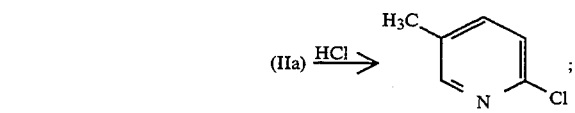

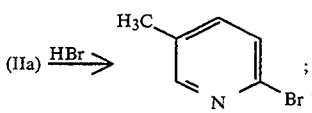

(IIa) 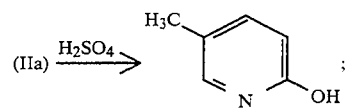 $\xrightarrow{H_2SO_4}$

The cyclistion here is demonstrated with the aid of ammonia, hydrogen chloride, hydrogen bromide or sulphuric acid. If the carboxylic acid ester group is employed instead of the cyano group (for Z) and ammonia is used for the cyclisation, the following exemplary reaction course is obtained in terms of formulae:

$H_3C-CH_2-CH=CH-COOCH_3 + HC[N(CH_3)_2]_3 \longrightarrow$

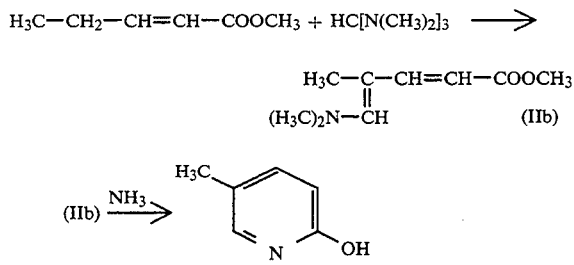

(IIb) $\xrightarrow{NH_3}$

The aminomethylenation can be carried out in all solvents whose acidity is lower than that of the 2-pentenoic acid derivative (III) or (IV) to be reacted; aminomethylenation with the aid of DMF acetal furthermore also takes place in alcohols as solvents. However, it is advantageous to work without solvents.

The 2-pentenoic acid derivative is employed at least in an equimolar ratio, relative to the ortho-amide. Preferably, however, the 2-pentenoic acid derivative is employed in a molar excess in order to utilise as completely as possible the expensive ortho-amide. Where the reaction is carried out without solvents, it is carried out in a very high molar excess of the 2-pentenoic acid derivative, which can be recovered after the aminomethylenation. The molar ratio which thus generally results is an amount from 1 to 50 mol of 2-pentenoic acid derivative per 1 mol of ortho-amide.

The aminomethylenation is carried out at a temperature from 50° to 200° C. and a pressure from 0.01 to 10 bar, preferably 0.1 to 3 bar, particularly preferably at 1 bar. For example, it is carried out at the boiling point of the 2-pentenoic acid derivative. It has proven advantageous to introduce the 2-pentenoic acid derivative initially, to bring to the desired reaction temperature and then to add the ortho-amide at the rate of its consumption; as a result, it is always present only in low concentrations and only gives rise to side reactions to a small extent. The easily volatile products formed in this reaction (amines, alcohols) are simultaneously removed by distillation. Where the 2-pentenoic acid derivative and the ortho-amide employed have boiling points lying close to one another, the ortho-amide, for example, can be fed into the middle of a packed column which is located above a bottom of boiling 2-pentenoic acid derivative. In a procedure of this type, the ortho-amide is reacted with the 2-pentenoic acid derivative inside the column; self-condensation products of the 2-pentenoic acid derivative which may be present remain in the bottom and are not available for reaction with the ortho-amide, as a result of which the formation of by-products is further decreased. This procedure is surprisingly convenient to favour the preferred γ-substituted propene derivative compared to the undesired α-substituted derivative.

After completion of the reaction, the desired aminomethylenated reaction product is recovered by vacuum distillation of the reaction bottom. For subsequent cyclisation, further purification can be dispensed with.

The γ-aminomethylenated 2-pentenoic acid derivative, preferably in its crude form, is cyclised for the cyclisation with an excess, for example one of 1 to 10 mol, of hydrogen chloride, hydrogen bromide, a concentrated strong inorganic or organic, non-oxidising oxygen acid or of $NH_3$. For this purpose, a polar solvent can be used, for example acetic acid, formic acid, chloroform, carboxamides or alcohols. The cyclisation is preferably carried out at a temperature from −10° C. to +25° C., preferably at 0° to 10° C. For example, the aminomethylenated 2-pentenoic acid derivative, in solid form or dissolved in one of the said solvents, is added dropwise to a solution of HCl or HBr in glacial acetic acid. Reverse addition is also possible. HCl or HBr gas can also be passed into the aminomethylenated 2-pentenoic acid derivative, this advantageously being present dissolved in one of the said solvents. HCl or HBr are preferably used in a molar excess of 1.5 to 5. By the analogous use of non-oxidising oxygen acids of the inorganic or organic series, the hydroxyl group can be introduced as the X substituent in the sense of the above reaction scheme. The analogous use of $NH_3$ leads to the introduction of amino as the X substituent. Oxygen acids which are suitable for this purpose are, for example, sulphuric acid, phosphoric acid, benzenesulphonic acid, p-toluenesulphonic acid and others known to the person skilled in the art. Reaction with $NH_3$ to give 2-aminopyridine is preferably carried out in alcohols, such as methanol, ethanol, propanol or butanol. Addition of alkoxide, e.g. sodium methoxide, can increase the reactivity of $NH_3$.

EXAMPLES

Example 1

50 ml of 98.7% strength cis-2-pentenenitrile from the distillation of 80% strength technical material (contains 1.1% of 2-methylbutene-2-nitrile) were heated to reflux in a 3-neck flask. 12.8 g of 97.3% strength methyl aminal ester (remainder DMF) were then slowly added dropwise. The mixture was heated under reflux for a further 2 h, the readily volatile constituents were stripped off in a rotary evaporator and a bulb tube distillation was carried out using the residue.

The distillate (19.7 g) was dissolved in 100 ml of glacial acetic acid, and dry HCl gas was passed in at 11° C. After 1 h at 5° C., the mixture was allowed to come to room temperature and to stand overnight. After concentration and the addition of toluene and water, the mixture was adjusted to pH 7–8. The organic phase was separated off and concentrated, and the residue was distilled. 2-Chloro-5-methylpyridine was obtained in 27.6% of the theoretical yield as a 98.6% pure material. The product was identified by GC (retention time) and GC-MS comparison with authentic material. $^1$H-NMR ($CDCl_3$): 2.3 d ($CH_3$), 7.22 ($H^3$), 7.48 ($H^4$), 8.62 ($H^6$) ppm.

Example 2

23 g of methyl trans-2-pentenoate were aminomethylated with 0.1 mol of methyl aminal ester analogously to Example 1 and the residue of the bulb tube distillation was dissolved in 100 ml of methanol. A further 20 ml of 30% strength sodium methoxide solution were added, 15 g of ammonia gas were passed in and the mixture was heated under reflux for 20 h. It was then diluted with 100 ml of water and adjusted to pH 4 with concentrated hydrochloric acid. HPLC analysis showed that 2-hydroxy-5-methylpyridine was formed in 42.6% of theory.

Example 3

120 g of trans-3-pentenenitrile and 0.3 g of hydroquinone monomethyl ether as stabiliser were initially introduced into a 500 ml one-neck flask fitted with a 1 m packed column and column head in 100 ml of isododecane and the mixture was heated under reflux. 30 g of ethyl aminal ester were added in the middle of the column with the aid of a metering pump in the course of 2 h. Readily volatile components were distilled off at the top of the column. The bottom was concentrated, excess pentenenitrile being recovered, and subjected to a bulb tube distillation. The proportion of "dimeric" pentenenitrile was higher than in Example 1, but the proportion of aminomethylenated "dimers" was reduced from 12.3 to 3.3% of the theoretical yield (relative to aminal ester).

Reaction with HCl/glacial acetic acid analogously to Example 1 gave 38.9% of 2-chloro-5-methylpyridine.

Example 4

Analogously to Example 3, cis-2-pentenenitrile was aminomethylenated with methyl aminal ester. The residue of the bulb tube distillation was diluted with 20 ml of glacial acetic acid and added dropwise to 300 ml of a 30% strength solution of HBr in glacial acetic acid. After working up, 43.3% of the theoretical yield of 2-bromo-5-methylpyridine were obtained.

Example 5

Analogously to Example 4, the residue was treated with 20 ml of concentrated sulphuric acid, the mixture was poured into water, and after working up 2-hydroxy-5-methylpyridine could be identified as the main product.

Example 6

Analogously to Example 1, cis-2-pentenenitrile was aminomethylenated using DMF acetal. After reaction with HCl/glacial acetic acid, 2-chloro-5-methylpyridine could be identified as the main product.

Example 7

Analogously to Example 3, cis-2-pentenenitrile was aminomethylenated with tris(dimethylamino)methane which was pumped into the upper third of the column.

The concentrated residue was diluted with glacial acetic acid and added dropwise at 5° C. to a saturated solution of HCl in glacial acetic acid. After customary working up, the product was obtained in 43.6% of the theoretical yield.

Example 8

Crude aminomethylenated cis-2-pentenenitrile from Example 7 was dissolved in THF and the solution was treated at 0° C. with aqueous 30% strength ammonia solution. After boiling under reflux for 6 h, 2-amino-5-methylpyridine was formed.

Example 9

Crude aminomethylenated cis-2-pentenenitrile from Example 7 was added dropwise at −10° C. to a saturated solution of HCl gas in chloroform/glacial acetic acid. By GC analysis using an internal standard, it could be shown that 2-chloro-5-methylpyridine was formed in 48.7% of the theoretical yield, relative to tris(dimethylamino)methane.

We claim:

1. A process for the preparation of 2-substituted 5-alkyl-pyridines of the formula

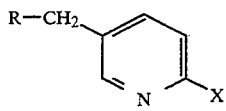

in which
R represents hydrogen or straight-chain or branched $C_1$–$C_4$-alkyl and
X denotes chlorine, bromine, hydroxyl or amino,
wherein a aminomethylenated 2-pentenoic acid derivative of the formula

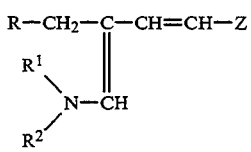

in which
$R^1$ and $R^2$ independently of one another represent straight-chain or branched $C_1$–$C_8$-alkyl, $C_2$–$C_8$-alkenyl, $C_2$–$C_8$-alkoxyalkyl, $C_3$–$C_8$-alkoxyalkenyl, $C_3$–$C_8$-cycloalkyl, $C_6$–$C_{12}$-aryl, $C_7$–$C_{10}$-aralkyl or a 5- to 8-membered saturated or unsaturated heterocyclic ring containing, 1 or 2 heteroatoms of which are selected from the group consisting of N, O and S, or where $R^1$ and $R^2$, together with the N atom which they substitute, form a 5- to 8-membered ring which optionally contains a further heteroatom from the group consisting of N, O and S, and
Z represents CN or $COOR^3$, where $R^3$ denotes straight-chain or branched $C_1$–$C_8$-alkyl, $C_2$–$C_8$-alkenyl, $C_2$–$C_8$-alkoxyalkyl, $C_3$–$C_8$-alkoxyalkenyl or $C_3$–$C_8$-cycloalkyl,
are cyclized optionally in the presence of a polar solvent and in the presence of
1 to 10 mol, relative to the 2-pentenoic acid derivative, of
HCl;
HBr; or
a concentrated strong inorganic or organic non-oxidizing oxygen acid;
or
1 to 10 mol, relative to the butene derivative, of $NH_3$.

2. The process according to claim 1, wherein said aminomethylenated 2-pentenoic acid derivative used is obtained by the reaction of a non-aminomethylenated 2-pentenoic acid derivative of the formula

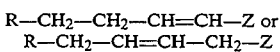

with an ortho-amide of the formula

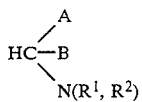

where
A and B independently of one another represent $OR^4$, $OR^5$, $N(R^6,R^7)$ or $N(R^8,R^9)$, wherein $R^4$, $R^5$, $R^6$, $R^7$, $R^8$ and $R^9$ independently of one another have the meaning of $R^1$ or $R^2$, in the presence or in the absence of a solvent whose acidity is lower than the C—H acidity of the 2-pentenoic acid derivative, at a temperature 50° to 200° C., and at a pressure 0.01 to 10 bar wherein the molar ratio of 2-pentenoic acid derivative to ortho-amide is 1 to 50:1.

3. The process according to claim 1, wherein R is hydrogen.

4. The process according to claim 1, wherein $R^1$ and $R^2$ independently of one another denote straight-chain or branched $C_1$-$C_8$-alkyl, cyclopropyl, cyclopentyl, cyclohexyl, phenyl or benzyl or together with the N atom which they substitute, form a 5- to 8-membered ring which optionally contains a further heteroatom from the group consisting of N, O and S.

5. The process according to claim 4, wherein $R^1$ and $R^2$ independently of another denote straight-chain or branched $C_1$-$C_4$-alkyl or together with the N atom which they substitute, form a morpholine, pyrrolidine or piperidine moiety, which is optionally substituted by $C_1$-$C_4$-alkyl or by hydroxy-$C_1$-$C_4$-alkyl.

6. The process according to claim 2, wherein the reaction is carried out at the boiling point of the 2-pentenoic acid derivative and is performed in an attached column with the ortho-amide being fed into said column.

7. The process according to claim 2, wherein the crude aminomethylenation product is cyclized.

8. The process according to claim 1, wherein the aminomethylated-2-pentenoic acid derivative is cyclized in the presence of HCl, HBr or a concentrated strong inorganic or organic non-oxidizing oxygen acid.

* * * * *